| United States Patent [19] | [11] 4,004,019 |
| Brand et al. | [45] Jan. 18, 1977 |

[54] INSECT CONTROL COMPOUNDS

[75] Inventors: William Wayne Brand, Hopewell; James Byron Lovell, Pennington, both of N.J.

[73] Assignee: American Cyanamid Company, Stamford, Conn.

[22] Filed: Sept. 12, 1975

[21] Appl. No.: 612,877

[52] U.S. Cl. .......................... 424/277; 260/240 R; 260/327 M

[51] Int. Cl.[2] ..................................... C07D 339/06

[58] Field of Search ................. 260/327 M, 240 R; 424/277

[56] References Cited

UNITED STATES PATENTS 3,766,208  10/1973  Lee et al. ...................... 260/327 M

*Primary Examiner*—Natalie Trousof
*Assistant Examiner*—C. M. S. Jaisle
*Attorney, Agent, or Firm*—H. G. Jackson

[57] ABSTRACT

The invention is novel hydrocarbon ethers of aminophenol derivatives, and their use in preventing the proliferation of insects by interfering with their normal development and growth pattern.

24 Claims, No Drawings

INSECT CONTROL COMPOUNDS

BACKGROUND OF THE INVENTION

1. Field of the Invention

The invention pertains to the pesticide art.

2. Description of the Prior Art

In contrast to most of the presently used pest control agents which act as contact or stomach poisons and dispatch insects rapidly, compounds of the present invention represented by formula I, below, or in more detail by formula II, below, markedly differ in their biological action on economically harmful insects belonging among others to the Orders of *Lepidoptera, Coleoptera* and Diptera; namely, the compounds of the present invention duplicate some of the morphogenic effects of a juvenile hormone by preventing maturation and proliferation of insect pests such as yellow mealworm (*Tenebrio molitor L.*) and Mexican bean beetle (*Epilachna varivestis Muls.*) by preventing or altering the growth and development of said insects in passing from one metamorphic stage to the next metamorphic stage; thus when larval or pupal stages of insects are brought in contact with or ingest compounds of type I, the normal development to the succeeding metamorphic stages is prevented, thus normal maturation is inhibited.

SUMMARY OF THE INVENTION

This invention relates to novel hydrocarbon ethers of aminophenol derivatives and a method of use thereof as insect control agents wherein the novel compounds prevent the maturation and/or proliferation of economically harmful insects. The compounds duplicate some of the morphogenic effects of juvenile-hormones and are also active as repellents and anti-feedants, and thus reduce or essentially eliminate foliar damage to economically important plants. The novel compounds of the invention are of the formula I

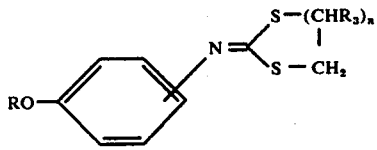

wherein *n* is 0 or 1, R represents a hydrocarbon chain of the following general structure:

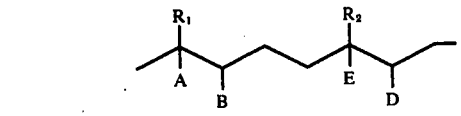

wherein $R_1$ and $R_2$ may be the same or different and are methyl or ethyl; A is hydrogen, halogen or alkoxy $C_1$–$C_4$; B is hydrogen; or A and B together may form a carbon-carbon bond, or A and B together may represent an "oxido" (-O-) bridge; E and D are hydrogen, or E and D together may form a carbon-carbon bond; and $R_3$ is hydrogen or methyl.

DETAILED DESCRIPTION OF THE INVENTION

The novel hydrocarbon ethers of aminophenol derivatives of the invention are represented by formula I below:

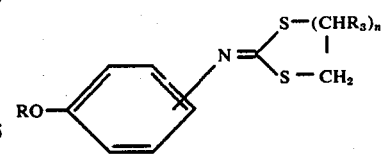

wherein *n* is 0 or 1, R represents a hydrocarbon chain of the following general structure:

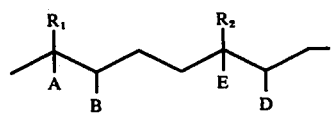

wherein $R_1$ and $R_2$ may be the same or different and are methyl or ethyl; A is hydrogen, halogen or alkoxy $C_1$–$C_4$; B is hydrogen; or A and B together may form a carbon-carbon bond, or A and B together may represent an "oxido" (-O-) bridge; E and D are hydrogen; or E and D together may form a carbon-carbon bond; and $R_3$ is hydrogen or methyl. The compounds may be prepared by the following reaction scheme graphically illustrated below:

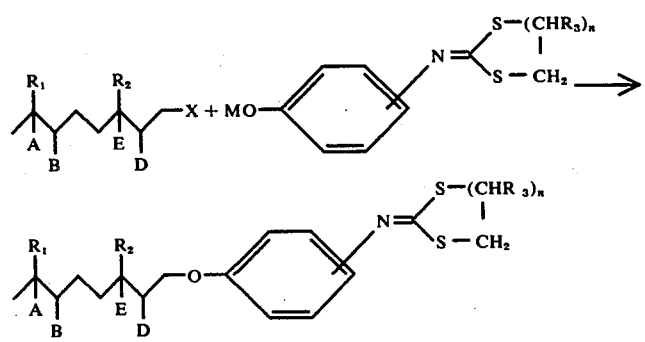

wherein *n*, $R_1$, $R_2$, $R_3$, A, B, E and D are defined as above; M is a monovalent alkaline earth metal; and X is a leaving group such as halogen or methanesulfonate. The formation of ethers by the above-illustrated reaction scheme is well known in the art and is usually carried out in the presence of a suitable solvent of acetone, methyl ethyl ketone, methylene chloride, chloroform, ethylene dichloride, dimethylformamide, dimethylacetamide, benzene, toluene, xylene, chlorobenzene, and the like. Advantageously the procedure to be used in the preparation of compounds of formula I (illustrated in more detail as formula II) may consist of:

a. adding the halogen or methanesulfonate derivative of R, where R is defined as above, or a solution thereof, to a solution or to a mixture of the phenol and an alkaline earth hydroxide dispersed in a suitable solvent selected from the solvents, in about equimolar amounts at temperatures ranging from about 20° C. to the boiling point of the solvent selected, holding the reactants together till the reaction is essentially complete as may be determined by testing for the presence or absence of the "phenol" or by the presence of $X^-$; or b. the procedure described in detail under (a) above is used, except a mixture of the phenol and an alkaline earth hydroxide dispersed in a suitable solvent is added to a solution of a halogen or methanesulfonate derivative of R.

The compounds thus obtained may be recovered from the reaction mixture and purified by standard laboratory procedures well known in the art, e.g. precipitations, crystallizations, extractions, vacuum distillations, chromatography, and the like.

This invention further relates to a method of use of the described compounds of type I, whereby the compounds of type I may be used to advantage as maturation inhibitors of economically harmful insects, since these compounds prevent or alter the growth and development of insects in passing from one metamorphic stage to the next metamorphic stage. Economically harmful insects which may be effectively controlled by the compounds of the present invention are among others Coleoptera [e.g. stored-grain pests, Mexican bean beetle (*Epilachna varivestis* Muls.), yellow mealworm (*Tenebrio molitor* L.)], Diptera (e.g. housefly, mosquito) and Lepidoptera [e.g. Southern armyworms (*Spodoptera eridania*, Cramer)].

The compounds of type I also act as repellents and/or anti-feedants and have been demonstrated to protect foliage from insect damage by inhibiting the feeding of insects and by repelling said insects from the feeding surface.

The compounds of the present invention represented by formula I, and in more detail by formula II, below:

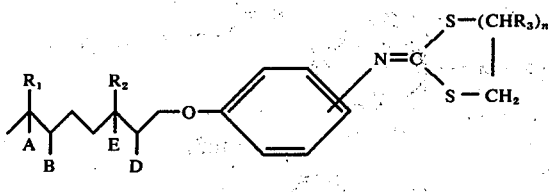

wherein R, $R_1$, $R_2$, A, B, E, D and n are defined as above, may be advantageously utilized by contacting the pupae, or their hosts, feed or habitat of insect larvae or pupae with dusts, sprays, fogs, dips, drenches, and the like, containing said compounds of the present invention in the range of from 1 ppm to 1000 ppm, preferably in the range of from 10 ppm to 300 ppm.

In practice, the active compounds of the present invention may be formulated as emulsifiable concentrates, dusts, dust concentrates, wettable powders, and the like.

Emulsifiable concentrates may be prepared by dissolving or dispersing about 10% to 75% by weight of the active ingredient in a solvent of water, acetone, methyl ethyl ketone, methyl isobutyl ketone, toluene, xylene, chlorobenzene, cyclohexanone, and the like, in the presence of suitable emulsifiers, wetting and dispersing agents such as alkylbenzene-ethyleneoxide condensates, alkylnaphthalene sulfonates, sodium N-methyl-N-oleoyl taurate, and the like, in amounts of about 1% to about 5%.

Dusts and dust concentrates may be prepared by conventional methods, by blending the active compound with inert carriers such as attapulgite, bentonite, montmorillonite, calcium stearate, corn starch, and the like. Dusts usually contain from about 1% to about 15% by weight of active ingredient, while dust concentrates may contain from about 16% to about 85% by weight of active ingredient. Wettable powders may be formulated similarly, except that such formulations usually contain wetting agents in amounts of about 0.1% to 2% by weight to achieve dispersion of the powder in water.

Emulsifiable concentrates and wettable powders are easily diluted with water, and upon dilution may be applied with commercially available equipment to the larvae, pupae, or to their hosts, habitat or feed. Applied to the hosts, feed or habitat, said active compounds repel and/or deter said insects; however, if some of the active compound is ingested by the insect larvae before repellency occurs, the thus-ingested active compound may interfere with the normal metamorphic processes and prevent maturation and/or proliferation of said insects. The normal metamorphic processes may also be interfered with if the insect larvae or pupae are brought in contact with said active compounds, and thus the maturation and/or proliferation of said insects will be prevented.

The following non-limiting examples are given to illustrate the preparation, repellent, deterrent and biological, juvenile and hormone-like activity of the compounds of the present invention represented by formulas I and II.

EXAMPLE 1

Preparation of Imidocarbonic acid, {p-[(3,7-dimethyl-2,6-octadienyl)oxy]phenyl dithio-,}cyclic methylene ester.

p-Hydroxphenyliminodithietane (7.88 g, 0.04 mol), sodium hydroxide (1.6 g, 0.04 mol) and dimethylformamide (200 ml) are mixed and stirred. Then geranylbromide (8.68 g, 0.04 mol) is added dropwise over 2 minutes. There is a slight exotherm, manifested by a temperature rise from 26° C to 30° C in about 10 minutes. The reaction mixture is stirred overnight, poured into water (400 ml) and extracted with ether (3 × 100 ml). The ether fractions are combined, washed with water, then with saturated sodium carbonate solution. The ether solution is dried and evaporated to dryness. The residue is stirred with hexane and filtered. The hexane solution is evaporated to dryness. The product, a brown oil, weighs 8.46 g (66.6% yield of theory).

EXAMPLES 3 to 11

Using the procedure of Example 1, the following compounds are prepared from the appropriate alkylating agent and appropriate phenol:

| Example Number | Alkylating Agent | Product |
| --- | --- | --- |
| 3 | (structure)—Br | (structure) |
| 4 | (structure, OC$_2$H$_5$)—Cl | (structure, OC$_2$H$_5$) |
| 5 | (structure)—OSO$_2$CH$_3$ | (structure) |
| 6 | (structure)—OSO$_2$CH$_3$ | (structure) |
| 7 | (structure, OC$_2$H$_5$)—OSO$_2$CH$_3$ | (structure, OC$_2$H$_5$) |
| 8 | (structure, OC$_2$H$_5$)—OSO$_2$CH$_3$ | (structure, OC$_2$H$_5$) |
| 9 | (structure, OC$_2$H$_5$)—OSO$_2$CH$_3$ | (structure, OC$_2$H$_5$) |
| 10 | (structure, Cl)—Cl | (structure, Cl) |
| 11 | (structure, Cl)—Cl | (structure, Cl) |

EXAMPLE 2

Preparation of Imidocarbonic acid, {p-[(6,7-epoxy-3,7-dimethyl-2-octenyl)oxy]phenyl-} dithio-, cyclic methylene ester Imidocarbonic acid, {p-[(3,7-dimethyl-2,6-octadienyl)oxy]phenyl}dithio-, cyclic methylene ester (6.25 g, 0.02 mol) is dissolved in methylene chloride (50 ml), the solution chilled to 0° C and a solution of m-chloroperbenzoic acid (4.06 g, 0.02 mil; 85% pure) in methylene chloride (50 ml) added slowly. The reaction mixture is held at 0° C for 30 minutes, then stirred an additional 90 minutes at room temperature. The reaction mixture is filtered, concentrated and the residue extracted with ether. The ether solution is washed with saturated sodium carbonate solution, dried and evaporated to dryness. The crude product is purified on a silica gel dry column, developed with a 2:1 mixture of methylene chloride:hexane.

EXAMPLE 12

Preparation of 2(4-Hydroxyphenyl)imino-1,3-dithiolane

A mixture of p-aminophenol (81.8 g, 0.75 mol), iminothiolane hydrochloride (116.7 g, 0.75 mol) and ethanol (1500 ml) is stirred and heated at reflux overnight. Charcoal and hyflo are then added to the reaction mixture and it is filtered hot. The filtrate is cooled overnight, the crystallized product filtered off yielding 34.5 g, as a tan solid. Additional product is obtained by washing the filter cake from the above hot filtration with 10% potassium hydroxide solution (600 ml). The solution is neutralized with concentrated hydrochloric acid and the precipitated product filtered. The combined yield is 95.8 g (60% of theory) of a tan solid, melting point 204° C to 208° C.

EXAMPLE 13

Preparation of Triethylammonium 4-Hydroxydithiocarbanilate

A solution of carbon disulfide (13.8 g) in absolute ethanol (100 ml) is added to a mixture of triethylamine (18.5 g), p-aminophenol (20 g) and absolute ethanol (400 ml). After the addition is completed, the reaction exotherms from 24° C to 29° C over a period of one hour and a tan solid is formed. The mixture is stirred one additional hour, cooled and filtered. Yield 39.8 g, of a tan solid (76% of theory), melting point 214° C to 217° C.

EXAMPLE 14

Preparation of 2(4-Hydroxyphenyl)imino-1,3-dithietane

A solution of triethylammonium 4-hydroxydithiocarbanilate (28.6 g) in dimethylformamide (100 ml) is added to a mixture of methylene bromide (52.2 g), triethylamine (10.1 g) and dimethylformamide (200 ml) over a 15-minute period while the temperature is being kept below 30° C. The mixture is stirred overnight, poured into water and the aqueous mixture extracted with benzene. The benzene solution is washed, dried, and stripped to yield 12.5 g (63.5% of theory) crude product, as a brown solid. The crude product is dissolved in hot methanol (100 ml) and the solution allowed to stand in the cold one day to yield 4.9 g of a bone-white solid, melting point 162° C to 163° C.

EXAMPLE 15

Preparation of 1,7-Dichloro-3,7-dimethyloctane

Into a well stirred solution of citronellyl chloride (8-chloro-2,6-dimethyl-2-octene; 26.1 g, 0.15 mol) in glacial acetic acid (600 ml), hydrochloric acid gas is passed for 4 hours at room temperature. Pentane (300 ml) and water (150 ml) are then added, the mixture stirred and transferred to a separatory funnel with additional pentane and water. The layers are separated, and the pentane layer is washed with several portions of water followed by saturated sodium bicarbonate solution. The pentane layer is then dried, and the solvent evaporated giving a quantitative yield of the product, boiling point 90° C to 93° C at 1.9 mm.

EXAMPLE 16

Biological Evaluation of the Compounds of the Present Invention for Juvenile Hormone-like Activity The following evaluation procedure is used: Groups of ten yellow mealworm (*Tenebrio molitor*) pupae, 0 to 24 hours of age are placed in 9.0 cm petri dishes. Each pupa is treated topically on the tip of the abdomen with 0.96 μl of reagent grade acetone containing 10 μg of test compound. Treatments are made with a ¼ cc tuberculin syringe fitted with a No. 26 gauge hypodermic needle and driven by the spindle of a micrometer. At least thirty pupae are treated per dose, and each dose is administered on at least two different days. After treatment, the pupae are retained in the petri dish at about 80° F and 50 ±10% relative humidity. Adults start to emerge from the control pupae treated with reagent grade acetone only in about 7 to 8 days at which time observations commence.

Adults are examined for retention of juvenile (pupal) characters such as gin traps on the lateral side of the abdomen, urogomphi on the tip of the abdomen, and pupal cuticle. The extent to which juvenile characters are retained depends on the effectiveness of the compound.

The rating system to determine the effectiveness of the compound is as follows:

0 = Perfect adult, no juvenile hormone activity.
1 = Retention of either gin traps or urogomphi.
2 = Retention of both gin traps and urogomphi.
3 = Retention of both gin traps and urogomphi plus retention of pupal cuticle around area of treatment.
4 = Second pupa; retention of all pupal characteristics.

The rating number is an average of the observations on at least 30 test insects.

+ = Higher rating then number given; i.e. some of the pupae present were rated at the next higher number.

The data obtained are summarized in Table I below.

TABLE I

Evaluation of Juvenile Hormone-like Activity on Yellow Mealworm (Tenebrio molitor) Pupa*

| Structure | 50.0 | 10.0 | 3.0 | 1.0 | 0.3 | 0.1 | 0.03 | 0.01 | 0.003 | 0.001 | 0.0001 |
|---|---|---|---|---|---|---|---|---|---|---|---|
| Structure 1 (OH-substituted) | | 4 | | | 3+ | 3 | 2+ | 2 | 1+ | ½ | |
| Structure 2 | | | | 3 | 2+ | 2 | 2 | | | | |
| Structure 3 (OC₂H₅) | | 4 | 4 | 3+ | 3 | 3 | 2+ | 2 | 2 | | |
| Structure 4 (OC₂H₅) | 4 | | | 4 | | 4 | 3 / 3 | | | 1 | 1 |

TABLE I-continued

Evaluation of Juvenile Hormone-like Activity on Yellow Mealworm (Tenebrio molitor) Pupa*

| Structure | Yellow Mealworm-μg/Pupa | | | | | | | | | |
|---|---|---|---|---|---|---|---|---|---|---|
| | 50.0 | 10.0 | 3.0 | 1.0 | 0.3 | 0.1 | 0.03 | 0.01 | 0.003 | 0.001 | 0.0001 |
| [structure: prenyl-O-C6H4-N=C(S-CH2-S) dithietane] | 3 | 2+ | | | | | | | | |
| [structure: prenyl-O-C6H4-N=C(S-CH2CH2-S) dithiolane] | | ½ | | | | | | | | |
| [structure: OC2H5-prenyl-O-C6H4-N=C(S-CH2CH2-S)] | 4 | 4 | 4 | 1 | | 0 | | | | |
| [structure: prenyl-O-C6H4(meta)-N=C(S-CH2CH2-S)] | | | | | | | | | | |

*At least 30 yellow mealworm pupae, 0 to 24 hours of age, are used at each dosage level.

EXAMPLE 17

Bilological Evaluation of the Compounds of the Present Invention for Insect Control Activity The following evaluation procedure is used: Sieva lima bean plants (two per pot) with primary leaves 3 to 4 inches long, are dipped in a solution containing 300 ppm of test compound, and are allowed to dry. One leaf is removed from the plant and placed in a 4-inch petri dish containing a moist filter paper on the bottom and ten last-instar larvae (13 days from hatching) of Mexican bean beetle (*Epilachna varivestis*). The day after treatment, another leaf is removed from the plant and is fed to the larvae after the remains of the original leaf are removed. Two days after treatment, the third leaf is fed to the larvae, and this is usually the last leaf needed. However, the fourth leaf is used on the third day if the larvae have not finished feeding. After the last-instar larvae ceased feeding, they are retained in the petri dish for transformation to the pupal stage from which the adults emerge. The petri dishes are held at about 80° F and 50 ±10% relative humidity. Normal adults usually start to emerge nine days after the beginning of the test. After normal emergence is completed, each dish is examined for dead larvae, pupae or adults; deformed pupae or adults; larval-pupal intermediates or pupal-adult intermediates; or any other interference with normal molting, transformation and emergence of pupae or adults. Compounds killing or affecting more than 50% of the insects are rerun at 100 ppm and further tested at 10 ppm. The rating system for activity is as follows:

0 = No effect.
1 = Reduced feeding - trace to light damage.
2 = 40-84% Deformed insects.
3 = 85-100% Deformed insects.
5 = 41-60% Killed.
6 = 61-70% Killed.
7 = 71-80% Killed.
8 = 81-99% Killed.
9 = 100% Killed.

The test data obtained are summarized in Table II below:

TABLE II

Evaluation of Juvenile Hormone-like Activity on Mexican Bean Beetle Larvae (*Epilachna varivestis*)*

| Structure | Mexican Bean Beetle Larvae Conc. ppm | | | |
|---|---|---|---|---|
| | 1000 | 300 | 100 | 10 |
| [structure: keto-prenyl-O-C6H4-N=C(S-CH2-S)] | | 3 | 3 | 0 |
| [structure: prenyl-O-C6H4-N=C(S-CH2CH2-S)] | 3 | 3 | 2 | |
| [structure: OC2H5-prenyl-O-C6H4-N=C(S-CH2CH2-S)] | | 3 | 5 | |

TABLE II-continued

Evaluation of Juvenile Hormone-like Activity
on Mexican Bean Beetle Larvae (Epilachna varivestis)*

| Structure | Mexican Bean Beetle Larvae Conc. ppm | | | |
|---|---|---|---|---|
| | 1000 | 300 | 100 | 10 |
| [structure: OC₂H₅-substituted chain-O-phenyl-N=dithietane] | | 3 | 3 2 | 0 |
| [structure: alkenyl chain-O-phenyl-N=dithietane] | | 8 | 3 2 | 0 |
| [structure: OC₂H₅-substituted chain-O-phenyl-N=dithiolane] | | 3 | 2 | 0 |
| [structure: alkenyl chain-O-phenyl (meta)-N=dithiolane] | | 6 | 0 | |
| [structure: Cl-substituted chain-O-phenyl-N=dithietane] | | | 2 | |
| [structure: Cl-substituted chain-O-phenyl-N=dithietane] | | 3 | | |

*Ten last-instar larvae (13 days from hatching) are used at each level of concentration.

EXAMPLE 18

Evaluation of Representative Compounds of the Present Invention as Repellents and/or Anti-Feedants This experiment is designed to establish a system within which the larval selection or rejection of food would indicate repellent, anti-feeding or feeding reduction activity on the part of the test compounds.

Test procedure: the choice chamber consists of a 150 mm × 15 mm petri dish with moist Whatman's No. 1 filter paper on the bottom. Young Sieva lima bean plants with two primary leaves and the first cluster of trifoliate leaves just starting to unfold[a] are sprayed with the test compounds in 65% acetone/35% water at the concentration given in Table III. A DeVilbiss atomizer is used to spray both the lower and upper surfaces until run-off. After the plants are dried for 2 hours, a primary leaf is excised and placed in the petri dish on the left side. An untreated leaf is placed on the right side. Twenty-five newly hatched (neonatal) Southern armyworms [Spodoptera eridania (Cramer)] are placed in a circle drawn on the bottom of the petri dish equidistant from both the treated and untreated leaves. The dishes are held at about 80° F and 50 ±10% r.h. Observations are made 1, 4, 6 and 8 days thereafter.

The data and observations are presented in Table III below.

TABLE III

Repellent and Deterrent Affects of Insect Growth Regulators
on Plant Surface to Southern Armyworms (Spodoptera eridania [Cramer])*

| | Conc in Compound ppm | Number of Days After Treatment 1 | | | | | |
|---|---|---|---|---|---|---|---|
| | | Live Southern Armyworms Actually on Leaves | | Southern Armyworms in Dish but not on Leaves | | Total Southern Armyworms Found | Southern Armyworms Unaccounted For |
| | | Treated Left Leaf | Untreated Right Leaf | Live | Dead | | |
| Control A: Two Untreated Leaves | — | 23 Insects on leaves | | 0 | 0 | 23 | 2 |
| [structure: chain-OC₂H₅-O-phenyl-N=dithietane] | 1000 | 2 | 11 | 0 | 6 | 19 | 6 |
| | 2000 | 3 | 12 | 4 | 4 | 23 | 2 |
| | 4000 | 6 | 6 | 3 | 7 | 22 | 3 |

TABLE III-continued

Repellent and Deterrent Affects of Insect Growth Regulators on Plant Surface to Southern Armyworms (Spodoptera eridania [Cramer])*

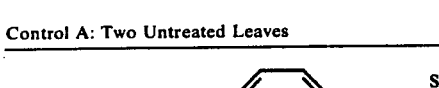

| | | Number of Days After Treatment 1 | | | | | |
|---|---|---|---|---|---|---|---|
| | | Live Southern Armyworms Actually on Leaves | | Southern Armyworms in Dish but not on Leaves | | Total Southern Armyworms | Southern Armyworms Unaccounted |
| | Conc in ppm | Treated Left Leaf | Untreated Right Leaf | Live | Dead | Found | For |
| Control A: Two Untreated Leaves | — | 23 Insects on leaves | | 0 | 0 | 23 | 2 |
| | 1000 | 0 | 18 | 1 | 4 | 23 | 2 |
| | 2000 | 0 | 19 | 0 | 4 | 23 | 2 |
| | 4000 | 1[a] | 11 | 1 | 0 | 25 | 0 |
| Control B: Two Untreated Leaves | — | 20 Insects on Leaves | | 1 | 4[b] | 25 | 0 |

*Twenty-five neonatal Southern armyworms introduced at Day 0 of test at each level of concentration of test compound and of controls.

| | | Number of Days After Treatment 4 | | | | | |
|---|---|---|---|---|---|---|---|
| | | Live Southern Armyworms Actually on Leaves | | Southern Armyworms in Dish but not on Leaves | | Total Southern Armyworms | Southern Armyworms Unaccounted |
| Compound | Conc. in ppm | Treated Left Leaf | Untreated Right Leaf | Live | Dead | Found | For |
| Control A: Two Untreated Leaves | — | 10 Insects on Leaves | | 11 | 0 | 21 | 2 |
| | 1000 | 4 | 4 | 5 | 0 | 13 | 0 |
| | 2000 | 0 | 3 | 6 | 5 | 14 | 5 |
| | 4000 | 0[c] | 6 | 7 | 0 | 15 | 0 |
| | 1000 | 2 | 8 | 7 | 1 | 19 | 1 |
| | 2000 | 0 | 8 | 9 | 0 | 19 | 2 |
| | 4000 | 0 | 4 | 9 | 0 | 13 | 0 |
| Control B: Two Untreated Leaves | — | 10 Insects on Leaves | | 8 | 0 | 18 | 3 |

| | | Number of Days After Treatment | | | | | |
|---|---|---|---|---|---|---|---|
| | | 6 | | | 8 | | |
| | | Southern Armyworms in Dish | | Southern Armyworms Unaccounted | Southern Armyworms in Dish | | Southern Armyworms Unaccounted |
| Compound | Conc. in ppm | Live | Dead | For | Live | Dead | For |
| Control A | — | 19 | 0 | 2 | 5 | 10 | 4 |
| | 1000 | 13 | 0 | 0 | 12 | 0 | 1 |
| | 2000 | 9 | 0 | 5 | 9 | 0 | 0 |
| | 4000 | 6 | 0 | 9 | 6 | 0 | 0 |
| | 1000 | 17 | 1 | 1 | 12 | 0 | 5 |
| | 2000 | 19 | 0 | 0 | 17 | 0 | 2 |
| | 4000 | 13 | 0 | 0 | 3 | 9 | 1 |
| Control B | — | 18 | 0 | 0 | 15 | 0 | 3 |

[a]Plus 12 dead.
[b]Crushed between lid and bottom.
[c]Plus 2 dead.
*The Southern armyworms were generally wandering and were not congregating at any particular location.

We claim:
1. A compound of the formula:

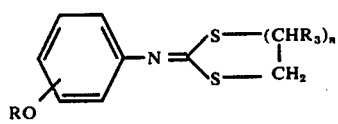

wherein $n$ is 0 or 1; R is a hydrocarbon chain of the following general structure:

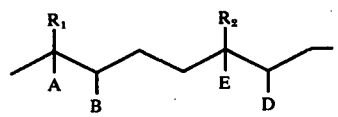

wherein $R_1$ and $R_2$ are methyl or ethyl; A is hydrogen, halogen or alkoxy $C_1$–$C_4$; B is hydrogen; or A and B together form a carbon-carbon bond, or A and B together represent an "oxido" (-0-) bridge: E and D are hydrogen; or E and D together form a carbon-carbon bond; and $R_3$ is hydrogen or methyl.

2. A compound according to claim 1: imidocarbonic acid, {p-[(3,7-dimethyl-2,6-octadienyl)oxy]phenyl} dithio-, cyclic methylene ester.

3. A compound according to claim 1: imidocarbonic acid, {p-[(6,7-epoxy-3,7-dimethyl-2-octenyl)oxy]phenyl}dithio-, cyclic methylene ester.

4. A compound according to claim 1, imidocarbonic acid, {p-[(3,7-dimethyl-6-octenyl)oxy]phenyl}dithio-, cyclic methylene ester.

5. A compound according to claim 1: imidocarbonic acid, {p-[(7-ethoxy-3,7-dimethyl-2-octenyl)oxy]phenyl}dithio-, cyclic methylene ester.

6. A compound according to claim 1: imidocarbonic acid, {p-[(7-ethoxy-3,7-dimethyloctyl)oxy]phenyl} dithio-, cyclic methylene ester.

7. A compound according to claim 1: imidocarbonic acid, {p-[(3,7-dimethyl-2,6-octadienyl)oxy]phenyl} dithio-, cyclic ethylene ester.

8. A compound according to claim 1: imidocarbonic acid, {p-[7-ethoxy-3,7-dimethyloctyl)oxy]phenyl} dithio-, cyclic ethylene ester.

9. A compound according to claim 1: imidocarbonic acid,{ m-[(3,7-dimethyl-6-octenyl)oxy]phenyl}dithio-, cyclic ethylene ester.

10. A compound according to claim 1: imidocarbonic acid, {m-[(7-ethoxy-3,7-dimethyloctyl)oxy]phenyl}dithio-, cyclic ethylene ester.

11. A compound according to claim 1: imidocarbonic acid, {p-[(7-chloro-3,7-dimethyloctyl)oxy]phenyl}dithio-, cyclic methylene ester.

12. A compound according to claim 1: imidocarbonic acid, {p-[(7-chloro-3,7-dimethyloctyl)oxy]phenyl}dithio-, cyclic ethylene ester.

13. A method of controlling insects of the order Lepidoptera, Coleoptera, and Diptera through antifeedant or repellant activity, or by inhibition of maturation of insects by contacting the larvae or pupae of the insects, or their hosts, feed or habitat with biologically active amounts of a compound of formula I:

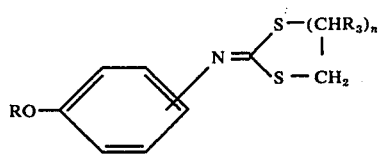

wherein $n$ is an integer of 1 or 2; R is a hydrocarbon chain of the following general structure:

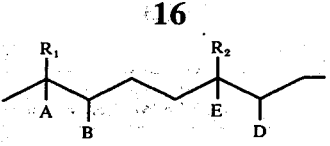

wherein $R_1$ and $R_2$ are methyl or ethyl; A is hydrogen, halogen, or alkoxy $C_1$–$C_4$; B is hydrogen; or A and B together form a carbon-carbon bond, or A and B together represent an "oxido" (-O-) bride, E and D are hydrogen, or E and D together form a carbon-carbon bridge; and $R_3$ is hydrogen or methyl.

14. The method according to claim 13, wherein the active compound is imidocarbonic acid, {p-[(3,7-dimethyl-2,6-octadienyl)oxy]phenyl}dithio-, cyclic methylene ester.

15. The method according to claim 13, wherein the active compound is imidocarbonic acid, {p-[(6,7-epoxy-3,7-dimethyl-2-octenyl)oxy]phenyl}dithio-, cyclic methylene ester.

16. The method according to claim 13, wherein the active compound is imidocarbonic acid, {p-[(3,7-dimethyl-6-octenyl)oxy]phenyl}dithio-, cyclic methylene ester.

17. The method according to claim 13, wherein the active compound is imidocarbonic acid, {p-[(7ethoxy-3,7-dimethyl-2-octenyl)oxy]phenyl}dithio-, cyclic methylene ester.

18. The method according to claim 13, wherein the active compound is imidocarbonic acid, {p-[(7-ethoxy-3,7-dimethyloctyl)oxy]phenyl}dithio-, cyclic methylene ester.

19. The method according to claim 13 wherein the active compound is imidocarbonic acid, {p-(3,7-dimethyl-2,6-octadienyl)oxy]phenyl}dithio-, cyclic ethylene ester.

20. The method according to claim 13, wherein the active compound is imidocarbonic acid, {p-[(7-ethoxy-3,7-dimethyloctyl)oxy]phenyl}dithio-, cyclic ethylene ester.

21. The method according to claim 13, wherein the active compound is imidocarbonic acid, m-[(3,7-dimethyl-6-octenyl)oxy]phenyl dithio-, cyclic ethylene ester.

22. The method according to claim 13, wherein the active compound is imidocarbonic acid, {m-[(7-ethoxy-3,7-dimethyloctyl)oxy]phenyl}dithio-, cyclic ethylene ester.

23. The method according to claim 13, wherein the compound is imidocarbonic acid, {p-[(7-chloro-3,7-dimethyloctyl)oxy]phenyl}dithio-, cyclic methylene ester.

24. The method according to claim 13, wherein the compound is imidocarbonic acid, {p-[(7-chloro-3,7-dimethyloctyl)oxy]phenyl}dithio-, cyclic ethylene ester.

* * * * *